(12) United States Patent
Ray et al.

(10) Patent No.: US 8,106,188 B2
(45) Date of Patent: Jan. 31, 2012

(54) PROCESS FOR PREPARING OLANZAPINE FORM I

(75) Inventors: Uttam Kumar Ray, Hyderabad (IN); Sreenivasa Rao Pathuri, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 419 days.

(21) Appl. No.: 12/227,819

(22) PCT Filed: Jun. 1, 2006

(86) PCT No.: PCT/IB2006/001769
§ 371 (c)(1),
(2), (4) Date: Nov. 29, 2008

(87) PCT Pub. No.: WO2007/138376
PCT Pub. Date: Dec. 6, 2007

(65) Prior Publication Data
US 2009/0131658 A1    May 21, 2009

(51) Int. Cl.
*C07D 495/04*    (2006.01)
(52) U.S. Cl. .................................................... 540/557
(58) Field of Classification Search ............. 540/557
See application file for complete search history.

(56) References Cited

U.S. PATENT DOCUMENTS

| | | |
|---|---|---|
| 6,906,062 B2 | 6/2005 | Chhabada |
| 2007/0021605 A1 | 1/2007 | Keltjens |
| 2007/0066602 A1 | 3/2007 | Keltjens |
| 2007/0072845 A1 | 3/2007 | Rao |
| 2007/0173496 A1 | 7/2007 | Keltjens |
| 2007/0191348 A1 | 8/2007 | Kotar-Jordan |
| 2008/0009481 A1 | 1/2008 | Thakashinamoorthy |
| 2008/0161557 A1 | 7/2008 | Mesar |
| 2008/0188465 A1 | 8/2008 | Patel |
| 2008/0234479 A1 | 9/2008 | Muthukumaran |
| 2008/0312433 A1 | 12/2008 | Che |
| 2009/0005556 A1 | 1/2009 | Shastri |

FOREIGN PATENT DOCUMENTS

| | | |
|---|---|---|
| WO | WO 2005/107375 A2 | 11/2005 |
| WO | WO 2006/010620 A2 | 2/2006 |
| WO | WO 2006/102176 A2 | 9/2006 |
| WO | WO 2007/105225 A1 | 9/2007 |
| WO | WO 2007/144901 A1 | 12/2007 |
| WO | WO 2008/091169 A2 | 7/2008 |
| WO | WO 2008/139228 A2 | 11/2008 |

*Primary Examiner* — Brenda Coleman
(74) *Attorney, Agent, or Firm* — Jay R. Akhave

(57) ABSTRACT

An improved for preparing Olanzapine Form I of Formula 1 in the presence of one solvent or a mixture of solvents.

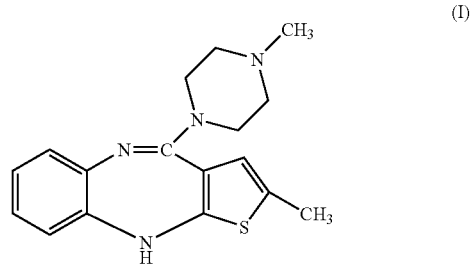

(I)

10 Claims, No Drawings

PROCESS FOR PREPARING OLANZAPINE FORM I

This application is the National stage of International Application No. PCT/IB2006/001769, filed on Jun. 1, 2006, which claims benefit under U.S.C §119 and 365(C), all of which are hereby expressly incorporated by reference into the present application.

FIELD OF THE INVENTION

The present invention relates to an improved process for preparing Form I of Olanzapine of Formula I.

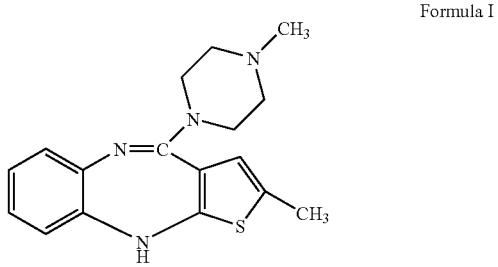

Formula I

BACKGROUND OF THE INVENTION

Olanzapine i.e. 2-Methyl-4-(4-methyl-1-piperazinyl)-10H-thieno[2,3-b][1,5]benzodiazepine of Formula I is an antipsychotic drug.

Olanzapine is an antagonist of dopamine D-1 and D-2 receptors, and in addition has antimuscarinic anticholinergic properties and antagonist activity at noradrenergic α-receptors. These properties indicate that the compound is a potential neuroleptic with relaxant, anxiolytic and anti-emetic properties, and may be useful in treating psychotic conditions such as, but not limited to, schizophrenia, schizophreniform diseases and mania. At lower doses the compound is indicated for use in the treatment of mild anxiety states.

In view of the importance of Olanzapine as an antipsychotic compound, several synthetic methods have been reported in the literature, which are as summarized below:

Olanzapine was first disclosed in U.S. Pat. No. 5,229,382. This patent does not refer to any specific polymorphic Form of Olanzapine. U.S. Pat. No. 5,736,541 patent claims Form II of Olanzapine. This patent also designated that the product obtained according to the process described in U.S. Pat. No. 5,229,382 is Form I.

U.S. Pat. No. 5,229,382 discloses a process in which the crude Olanzapine is prepared in acetonitrile at boiling temperatures.

U.S. Pat. No. 5,703,232 discloses a process to prepare Form I. The process comprising, suspending technical grade Olanzapine in acetone or tetrahydrofuran or ethyl acetate or t-butanol and heated to 60° C. while stirring the mixture was maintained for 30 min. The mixture was cooled to about 25° C. The resulting product was isolated using vacuum filtration. The product identified as Form I. In the same patent another process is described which comprises, dissolving alcoholate solvate of Olanzapine in different solvents to prepare Form I.

U.S. Pat. No. 5,637,584 discloses a process to prepare anhydrous Form I from Olanzapine methylene chloride solvate. The process comprises, drying or azeotroping the methylene chloride solvate and recrystallizing the material in an appropriate solvent in the presence of a Form I seed crystal to provide the desired Form I Olanzapine.

US 2004/0048854 claims a process to prepare Olanzapine Form I, which comprises reacting 4-amino-2-methyl-10H-thieno[2,3-b][1,5]benzodiazpine HCl and 1-methylpiperazine in an aprotic high boiling solvent or mixtures thereof (dimethyl sulfoxide, dimethylforamide, a mixture of dimethyl sulfoxide and toluene, or a mixture of dimethylforamide and toluene) at a temperature of between about 90 to 130° C.; purifying the product in acidic medium (acetic acid); basifying the product (sodium hydroxide) to a pH of between 7.5-9; and extracting the product using a low boiling organic solvent (diethylether, dichloromethane, dichloroethane, chloroform, ethyl acetate, other low polar ketonic solvents, and mixtures thereof) and Form I isolated.

US 2004/0067936 A1 claims a process to prepare Olanzapine Form I from Olanzapine dihydrate-I or Olanzapine monohydrate-I or Olanzapine Form II. The process comprising stirring from Olanzapine dihydrate-I or Olanzapine monohydrate-I or Olanzapine Form II in dichloromethane at reflux to obtain a clear solution. Then to the resulting solution carbon was added, followed by filtration and cooling the filtrate to 0-5° C. and stirring for 60-90 min. Then solid was separated and washed, and dried at 60-70° C. to a constant weight.

However, with the above reported processes, we noticed that Form I is not formed consistently. Hence, there is a need to develop a solvent/solvent system which gives Form I consistently.

OBJECTIVE

The objective of the present invention is to provide an improved process for preparing Olanzapine Form I consistently.

In yet another objective of the present invention is to provide an improved process for preparing of Olanzapine Form I, which is simple, industrially applicable and economically viable.

In yet another objective of the present invention is to provide an improved process for preparing of Olanzapine Form I, which is stable.

SUMMARY OF THE INVENTION

The present invention relates to an improved process for the preparation of Olanzapine Formula I,

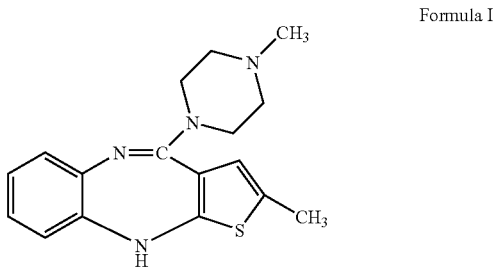

Formula I which comprises,
a) suspending the Olanzapine in an saturated hydrocarbon solvent,
b) heating the reaction mixture to reflux,
c) cooling the reaction mass and seeding with Form I, and
d) isolating the Olanzapine Form I precipitated by conventional methods.

In another embodiment of the present invention, optionally an alcoholic solvent is added to the reaction mixture before cooling.

DETAILED DESCRIPTION OF THE INVENTION

In yet another aspect of the present invention, Olanzapine was suspended in the hydrocarbon solvent and reaction mass was refluxed at a temperature ranging from 55-80° C., and stirred for 10-20 min. To the stirred reaction mass optionally alcoholic solvent was added to make the solution clear. Subsequently, the clear reaction mass was cooled to 50-60° C., and seeded with Form I. Further the reaction mass was cooled to 20-30° C., preferably 25° C. and stirred for 30 minutes at the same temperature to precipitate Olanzapine Form I. The resulting Olanzapine Form I was isolated by conventional methods.

In an aspect of the present invention, the Olanzapine used for preparing Olanzapine Form I is selected from technical grade Olanzapine or crude Olanzapine, which is prepared either by methods reported in prior-art.

In yet another aspect of the present invention, the saturated hydrocarbon solvent is selected from hexane, heptane, cyclopropane, cyclohexane, cycloheptane etc or mixtures thereof, preferably cyclohexane can be used.

In yet another aspect of the present invention, the alcoholic solvent is selected from methanol, ethanol, isopropanol, propanol, butanol etc, and mixtures thereof, preferably selected from ethanol.

The DSC, XRD and IR of the Olanzapine Form I matched with reported Form I data.

The invention is illustrated with the following examples, which are provided by way of illustration only and should not be construed to limit the scope of the invention.

Example 1

Preparation of Olanzapine Form I

Step-A:
Preparation of Crude 2-METHYL-4-(4-METHYL-1-PIPERAZINYL)-10H-THIENO[2,3-B][1,5]BENZODIAZEPINE 4-Amino-2-methyl-10H-thieno[2,3-b][1,5]benzodiazepine, hydrochloride (100 g) was refluxed in a mixture of N-methylpiperazine (349 mL), dimethylsulphoxide (465 mL) and toluene (465 mL) under a nitrogen atmosphere for 20 hours. The mixture was cooled to 50° C., and water (465 mL) was added at 50-55° C. in 20 min. Then the reaction mass was cooled to 5° C. and stirred for 2 h. The product was filtered and washed with water (100 mL, 20° C.). Dried the product at 60-70° C. under reduced pressure to give crude 2-Methyl-4-(4-methyl-1-piperazinyl)-10H-thieno[2,3-b][1,5]benzodiazepine or Olanzapine.

Yield: 113 g

Step-B:
Preparation of Olanzapine Form I

Crude Olanzapine (2.0 g) was suspended in cyclohexane (30 mL) and heated to reflux at 78-80° C. To the refluxed solution ethanol (10 mL) was added, to make the reaction mass clear. Heating was stopped and seeded with Form I (10 mg) at 58° C. The resulting hazy solution was further cooled to 25° C. and stirred for 30 min at 25±2° C. The resulting product was filtered and washed with a mixture of cylohexane and ethanol (3:1). Dried the product at 50-60° C. under reduced pressure to give Form I of Olanzapine.

Yield: 1.5 g

Example 2

Preparation of Olanzapine Form I

Step-A:
Preparation of Technical Grade 2-METHYL-4-(4-METHYL-1-PIPERAZINYL)-10H-THIENO[2,3-B][1,5]BENZODIAZEPINE 4-amino-2-methyl-10H-thieno[2,3-b][1,5]benzodiazepine, hydrochloride (50 g) was stirred in a mixture of N-Methylpiperazine (113 g) and Dimethylsulfoxide (300 mL) at 120° C. for 20 h under nitrogen atmosphere. The reaction mass was cooled to 20° C., followed by addition of methanol (500 mL) and the reaction mass was stirred for 30 min. Water (150 mL) was added at 20° C. in 25 min, and the reaction mass was cooled to 5° C. The reaction mass was stirred for 30 min at 0-5° C. The product was filtered and was washed with chilled methanol (50 mL, 5° C.). Dried the product at 50° C. under reduced pressure to give technical 2-Methyl-4-(4-methyl-1-piperazinyl)-10H-thieno[2,3-b][1,5]benzodiazepine or Olanzapine.

Yield: 50.5 g

Step-B:
Preparation of Olanzapine Form I

Technical grade Olanzapine (2.0 g) was suspended in cyclohexane (30 mL) and heated to reflux at 78-80° C. To the refluxed solution ethanol (10 mL) was added, to make the reaction mass clear. Heating was stopped and seeded with Form I (10 mg) at 58° C. The resulting hazy solution was further cooled to 25° C. and stirred for 30 min at 25±2° C. The resulting product was filtered and washed with a mixture of cylohexane and ethanol (3:1). Dried the product at 50-60° C. under reduced pressure to give Form I of Olanzapine.

Yield: 1.65 g

We claim:
1. An improved process for preparing Olanzapine Form I of Formula I

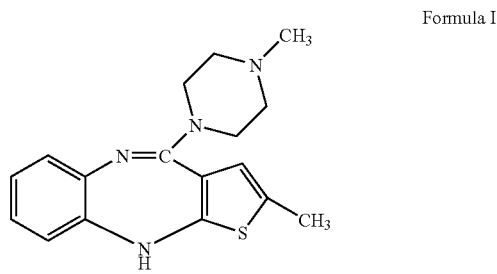

Formula I which comprises, a) suspending the Olanzapine in an saturated hydrocarbon solvent, b) heating the reaction mixture to reflux, c) cooling the reaction mass and seeding with Form I, and d) isolating the Olanzapine Form I precipitated by conventional methods.

2. The process according to claim 1, wherein an alcoholic solvent is added to the reaction mixture before cooling in step (c).

3. The process according to claim 1, wherein the Olanzapine used for preparing Olanzapine Form I is selected froth technical grade Olanzapine or crude Olanzapine.

4. The process according to claim 1, Olanzapine was suspended in the hydrocarbon solvent and reaction mass was refluxed at a temperature ranging from 55-80° C., and stirred for 10-20 min.

5. The process according to claim 1, wherein the reaction mass was cooled to 50-60° C., and seeded with Form I.

6. The process according to claim 2, wherein the reaction mass was cooled to 50-60° C., after addition of alcoholic solvent and seeded with Form I.

7. The process according to claim 1, wherein the saturated hydrocarbon solvent is selected from hexane, heptane, cyclopropane, cyclohexane, or mixtures thereof.

8. The process according to claim 1, wherein the saturated hydrocarbon solvent is cyclohexane.

9. The process according to claim 2, wherein the alcoholic solvent is selected from methanol, ethanol, isopropanol, propanol, butanol, and mixtures thereof.

10. The process according to claim 2, wherein the alcoholic solvent is ethanol.

* * * * *